United States Patent [19]

Weikel

[11] Patent Number: 4,468,199

[45] Date of Patent: Aug. 28, 1984

[54] DENTAL WEDGE

[76] Inventor: Gary Weikel, 1050 Greenfield Dr., El Cajon, Calif. 92021

[21] Appl. No.: 456,961

[22] Filed: Jan. 10, 1983

[51] Int. Cl.³ .............................................. A61C 7/00
[52] U.S. Cl. .................................................... 433/149
[58] Field of Search ................ 433/168, 149; 128/325, 128/326

[56] References Cited

U.S. PATENT DOCUMENTS

| | | | |
|---|---|---|---|
| 351,065 | 10/1886 | Miller . | |
| 421,952 | 2/1890 | Marshall . | |
| 486,112 | 11/1892 | Kuns . | |
| 532,722 | 1/1895 | Dennis . | |
| 1,568,054 | 1/1926 | Burlew . | |
| 2,396,203 | 3/1946 | Robinson | 128/325 |
| 2,629,930 | 3/1953 | Lane | 32/63 |
| 2,867,905 | 6/1953 | Meacham | 32/63 |
| 2,891,313 | 6/1959 | Crowley | 32/63 |
| 3,096,585 | 7/1963 | Dockum | 32/40 |
| 3,473,226 | 10/1969 | Arlers et al. | 32/64 |
| 3,510,948 | 5/1970 | Walthall | 32/64 |
| 3,636,631 | 1/1972 | Tofflemire | 32/64 |
| 3,815,243 | 6/1974 | Eames | 32/63 |
| 4,337,041 | 6/1982 | Harsany | 433/149 |

Primary Examiner—Robert Peshock
Attorney, Agent, or Firm—Fulwider, Patton, Rieber, Lee & Utecht

[57] ABSTRACT

An improved dental wedge is devised wherein a cross section of the dental wedge, perpendicular to the longitudinal axis of the dental wedge, is generally trapezoidal. The trapezoidal cross section is characterized by a minor base and an opposing major base and is connected by symmetric, sloping sides. The sloping sides of the trapezoidal cross section intersect the major base through flat intermediate portions whereby a sharp acute angle of the intersection between the sloping sides and major base is avoided. The dental wedge is impregnated with a hemostatic agent and has a tapered sled-like tip where the major base tapers upwardly to the minor base and terminates at the tip of the dental wedge in a flat, snub-nosed end. By reason of this combination of elements, the dental wedge can be inserted between and exert a maximum wedging force against each of two adjacent teeth and yet provide no substantial obstruction to a matrix band placed over either one of the teeth. The dental wedge bears directly against the teeth and does not require the matrix and dental wedge to be simultaneously worked between the teeth. The matrix band can be completely inserted over the tooth with the dental wedge fully inserted.

2 Claims, 7 Drawing Figures

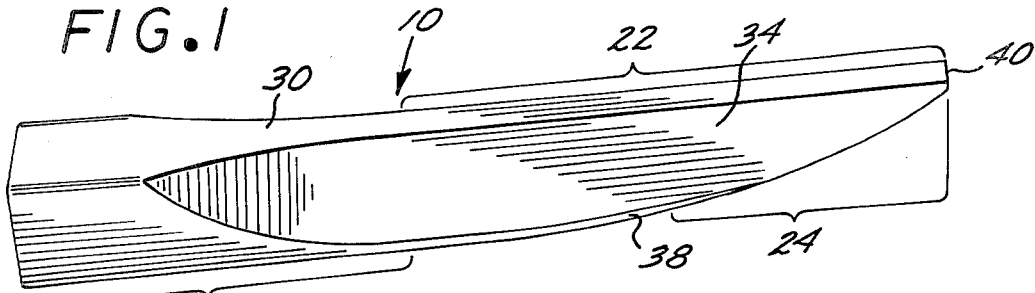
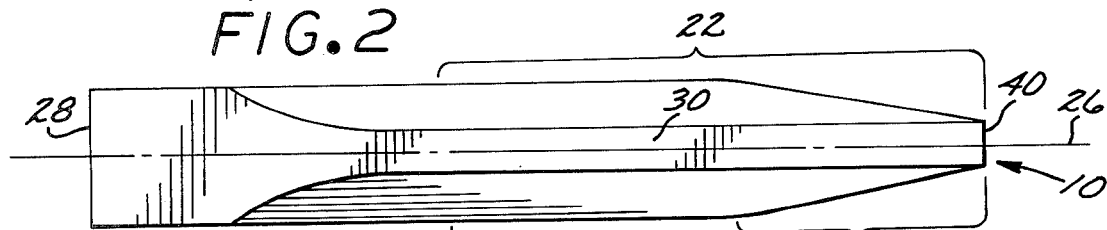
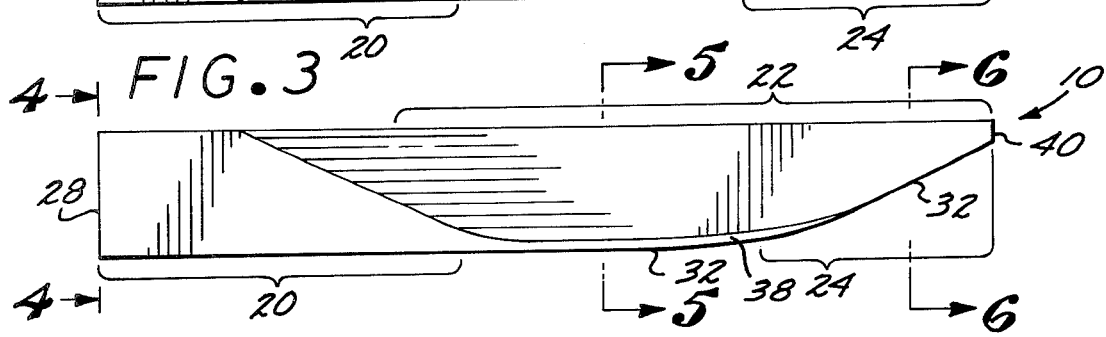
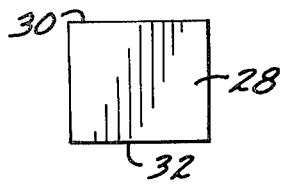
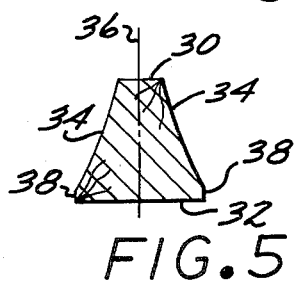
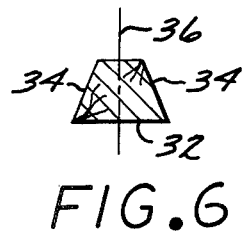
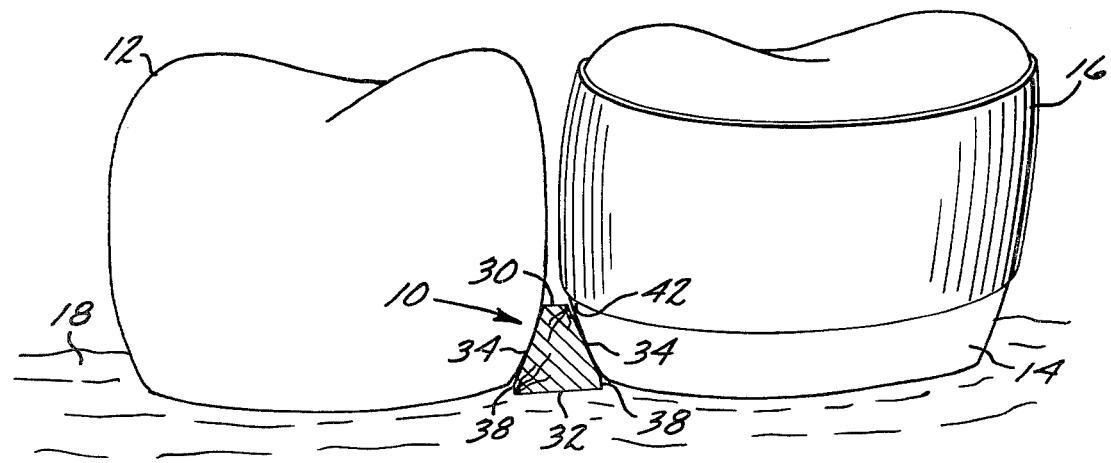

DENTAL WEDGE

BACKGROUND OF THE INVENTION

1. Field of the Invention

The present invention relates to the field of dental appliances and in particular to dental wedges for interproximal insertion to facilitate the use matrix bands.

2. Description of the Prior Art

When a cavity in a tooth is filled with an amalgam, it has been the practice in the prior art to insert a dental wedge between the teeth to faciliate the insertion of a matrix band over the tooth to be treated. Without such a matrix band, the soft amalgam alloy or silicon cement will flow out the open proximal side of the cavity. The dental wedge serves to spread the teeth to allow the insertion of the matrix band. The great variety of dental wedges which have been devised to meet this problem indicates not only the importance of this device, but the number of attempted solutions attests to the lack of a satisfactory, simple and practical wedge which has yet to be devised.

In particular, these prior art wedges have included various forms of triangular wedges, some with concave surfaces such as shown by Meacham, "Dental Wedge," U.S. Pat. No. 2,867,905; Walthall, "Dental Wedge," U.S. Pat. No. 3,510,948; Eames, "Wedge for Dental Matrix Bands," U.S. Pat. No. 3,815,243; Tofflemire, "Teeth Separating Wedges for Use During Filling Operations," U.S. Pat. No. 3,636,631; Burlew, "Tooth Wedge," U.S. Pat. No. 1,568,054; Dockum, "Tool for Inserting Dental Wedges," U.S. Pat. No. 3,096,585; and Arlers, et al, "Dentists' Wedge," U.S. Pat. No. 3,473,226. These prior art devices have various contours but each is characterized by a sculptured portion of the wedge, used for driving the teeth apart, which is generally characterized by a triangular or near triangular cross section perpendicular to the elongated, longitudinal axis of the wedge. As shown in Arlers, the triangular shaped wedge is placed between the band and tooth. However, one of the purposes of the wedge is to facilitate spreading of the teeth so that the matrix band can be more easily inserted. Eames, Walthall and Meacham each show a wedge with a triangular cross section in immediate contact with the matrix band. Thus, the matrix band and wedge have to be placed over and between the teeth respectively, more or less at the same time and worked into position as best as possible.

What is needed is a dental wedge which has a shape which will spread the teeth and yet allow easy insertion of the matrix band between the teeth after insertion of the wedge. Further, what is needed is a dental wedge which has a design less likely to cause cutting, tearing, bruising or other damage to the adjacent soft tissues of the gum and, which incorporates a means for inhibiting bleeding.

BRIEF SUMMARY OF THE INVENTION

The present invention is an improvement in a dental wedge for interproximal insertion between two teeth comprising an elongated solid body having a longitudinal axis and including a base portion and a sculptured portion. The sculptured portion has a cross section perpendicular to the longitudinal axis which is characterized as having a general trapezoidal shape defined by a minor base forming a top flat surface of the trapezoidal cross section and by a major base generally forming the flat bottom surface of the trapezoidal cross section. The minor and major bases are joined by symmetric, slightly concave side surfaces. The side surfaces join the major base through a flat, intermediate portion so that there is no point or sharp edge at the intersection of the side surfaces and the major base. The sculptured portion includes a tapered tip subportion and a blunted point so that the end of the sculptured portion, which is distal from the base portion, is terminated by a flat-ended surface. The major base of the sculptured portion is tapered upward through the tip subportion and intersects the flat-ended surface. By reason of this combination of elements, a dental wedge is devised that is easily inserted between the teeth, provides a maximal separating force between the teeth, and a minimal obstruction to a matrix band which maybe disposed on either one of the teeth above the wedge.

BRIEF DESCRIPTION OF THE DRAWINGS

FIG. 1 is a perpsective view of the dental wedge of the present invention.

FIG. 2 is a top elevational view of the dental wedge shown in FIG. 1.

FIG. 3 is a side elevational view of the dental wedge shown in FIG. 1.

FIG. 4 is an end view of the dental wedge as seen through line 4—4 of FIG. 3.

FIG. 5 is a sectional view taken through line 5—5 of FIG. 3.

FIG. 6 is a sectional view taken through line 6—6 of FIG. 3.

FIG. 7 is a sectional view of the dental wedge showing the wedge in a place between two teeth, one of which teeth is fitted with a matrix band.

The various embodiments and objects of the present invention are better understood when viewing the above-described Figures, wherein like elements are referenced by like numerals, in light of following detailed description of the preferred embodiments.

DETAILED DESCRIPTION OF THE PREFERRED EMBODIMENTS

The present invention is an improved dental wedge which can be inserted between two teeth and which facilitates the simultaneous or subqunt insertion of a matrix band and yet has sufficient force to separate the teeth without interfering with the matrix band.

Dental wedge 10 of the present invention is shown in cross sectional view in FIG. 7 inserted between two teeth 12 and 14 wherein tooth 14 has a matrix band 16 disposed about it. It is not necessary that matrix band 16 be wedged between dental wedge 10 and tooth 14 as is typical in the prior art. The shape of dental wedge 10, as described in more detail inconnections with FIGS. 1-6, permits the insertion of dental wedge 10 independently of the insertion of matrix band 16 and yet still has sufficient force to sufficiently separate closely packed teeth 12 and 14 which are firmly implanted in gum 18.

Referring now to FIG. 1, the specific, advantageous characteristics of dental wedge 10 can now be understood. The dental wedge, generally denoted by reference numeral 10, includes a base or nonsculptured portion 20 and a sculptured portion 22. The sculptured portion 22 is further characterized by a tip portion 24 described in greater detail in connection with FIG. 3.

Dental wedge 10 is formed of an elongated solid body having a longitudinal axis of symmetry 26 illustrated in FIG. 2, which Figure shows a top elevational view of wedge 10. As illustrated in FIG. 4, which shows an end view of wedge 10 as seen through line 4—4 of FIG. 3, wedge 10 is made from a stock of solid material having a generally rectangular or square cross section. Base end 28 of wedge 10 is a square, flat surface formed perpendicular to longitudinal axis 26.

Wedge 10 is made of a hardwood such as linen wood which is a variety of maple. However, it is entirely within the scope of the present invention that many other types of materials, such as synthetics or plastics could also be substituted.

Referring now to FIGS. 5 and 6, which are sectional views taken through lines 5—5 and 6—6 of FIG. 3 and in particular referring to FIG. 5, it can be seen that the cross section perpendicular to longitudinal axis 26 of wedge 10 at point in sculptured portion 22 is characterized by having a generally trapezoidal shape. For example, in FIG. 5 the perpendicular cross section is characterized by a minor base or top surface 30 and a major base 32 which are connected by symmetric side surfaces 34, which are symmetric about a vertical axis of symmetry 36. Side surface 34 is slightly concave as illustrated in FIG. 5. Furthermore, side surfaces 34 extend from minor base 30 downwardly toward major base 32 but do not directly intersect major base 32. The corners of the intersection between sides 34 and major base 32 have been removed to create a small, intermediate, flat surface 38 which forms the surface actually connecting the lower edge of sides 34 with the outer edges of major base 32. Thus, a cross section of wedge 10 through sculptured section 22 is actually a six-sided contour, two of which sides lie on surfaces which are nonplanar or concave.

Referring now to FIG. 6, a cross section taken through line 6—6 of tip portion 24 has substantially the same topological shape as a perpendicular cross section taken elsewhere through sculptured section 22 except that major base 32 has been sloped upwardly toward minor base 30 to form a sled-like shape as best shown in FIG. 3 and the flat surface 38 has terminated leaving angular corners.

Referring now to FIG. 3, major base 32 is tapered upward beginning at the left-hand edge of tip subportion 24. The taper continues upward to the end of wedge 10 distal from base end 28. The tip of wedge 10 is terminated by flat tip end 40 such that tapered base portion 32 and tip subportion 24 do not actually intersect minor base 30 but are only connected indirectly through a snub-nose or truncated tip end 40.

Referring now to FIG. 2, minor base 30 is shown as having a uniform width throughout the entire length of sculptured portion 22 and as beginning to flair outwardly at the righthand end of base portion 20. Approximately half way back through base portion 20, minor base 30 is flaired outward in width until it is equal to the entire width of wedge 10, or in other words to the width of base end 28 as illustrated in FIG. 4. Thus, minor base 30, beginning from the left end of wedge 10, as shown in FIG. 2, has a width equal to that of wedge 10 up to halfway through base portion 20, and then tapers down to a width of aproximately one-third the width of wedge 10 and maintains that width thoughout sculptured portion 22. On the other hand, major base 32 has a width as great as base end 28 as shown in FIG. 4, and, as best shown in FIG. 2, continues with that full width until tip subportion 24 at which time it tapers downwardly until it reaches the same width as minor base 30 at tip end 40 of wedge 10.

Although the present invention is made in several sizes with the proportions as described above, the dimension of one of the sizes is specified here as an illustrative example, but should not be taken as limiting the breadth or scope of the present invention. For example, wedge 10 is made from a hardwood maple rectangular stock 2 mm square in cross section with a finished length of 17 mm. The length of base portion 20 from base end 28 to the point at which minor base 30 just begins to decrease in width is approximately 2.5 mm with minor base 30 being approximately 0.5 mm wide and major base 32 being 2 mm wide.

Referring again to FIG. 7, the advantages and operation of the dental wedge of the present invention can better be described. Since the top of wedge 10 is truncated, there is no obstruction provided by wedge 10 to matrix band 16 which freely fits over the tooth 14 which has been separated from tooth 12 by wedge 10. In fact, minor base 30 in some instances may help to provide a dam to seal the soft amalgam or cement within matrix band 16 at the lower edge 42 of band 16 where it departs from the curvature of tooth 14, which amalgam or cement might otherwise ooze.

Yet, virtually no wedging force provided by wedge 10 to force teeth 12 or 14 apart is lost, since sides 34 are in contact with teeth 12 and 14 and since most of the wedging force is derived from contact with the lower portions of sides 34 rather than near the apex of a triangular wedge as in the prior art or even from upper portions of side 34 near minor base 30.

Furthermore, the linen wood wedge will indent slightly to accomodate the contour of the wedged apart teeth and will take a permanent set to cause the wedge to be maintained in position rather than being wedged out as would be the case for a wedge constructed of hard non-compressive materials.

In addition, bevelled edges 38, together with flat tip end 40, as illustrated in FIGS. 1-3, are provided to minimize the risk of cutting, tearing or puncturing soft gum tissue 18 when wedge 10 is inserted in the gap between teeth 12 and 14. The taper of major base 32 in tip subportion 24, allows wedge 10 to be inserted at angle to the longitudinal axes of teeth 12 and 14, rather than perpendicular thereto and rather than generally parallel to the occlusal gum surface. Wedge 10 is then forced between teeth 12 and 14 by conventional means and eventually assumes a generally perpendicular orientation to the longitudinal axes of teeth 12 and 14 as the lower surfaces of teeth 12 and 14 come to bear hard against sides 34 of wedge 10. Thus, the shape of wedge 10 allows the wedge to be "shoe-horned" between the teeth.

In the event that some bleeding should occur, wedge 10, when made of porous material such as maplewood, is also impregnated with a hemostatic agent, namely a solution of racemic epinephrine hydrochloride. Approximately 0.1 to 0.8 milligrams of solution will be absorbed and retained by wedge 10, depending upon the size of the wedge and normal process variations. If the forcing of wedge 10 between teeth 12 and 14 causes a slight abrasion between wedge 10 and the gum, the impregnated hemostatic agent within wedge 10 will assist to inhibit any bleeding. The crushing force to which the porous material of the wedge is subjected thereby forces the hemostatic agent from the wedge as it is inserted.

It must be understood that many modifications and alterations may be made by those having ordinary skill in the art without departing from the spirit and scope of the present invention. The embodiments described above have been illustrated only for the purposes of example and should not be taken as limiting the invention as set forth in the following claims.

I claim:

1. An improvement in a dental wedge for interproximal insertion between two teeth and gums comprising an elongated and porous solid body impregnated with a hemostatic solution including a base portion and a sculptured portion, said sculptured portion having a cross section perpendicular to the longitudinal axis of said elongated solid body, said cross section having a generally trapezoidal shape defined by a minor base forming the top surface of said trapezoidal-shaped cross section and defined by a major base generally forming the bottom flat surface of said trapezoidal-shaped cross section, said minor and major bases being joined by symmetric, slightly concave side surfaces, said side surfaces joining said major base through a flat intermediate portion, said sculptured portion including a tapered tip subportion and a blunted point so that the end of said sculptured portion distal from said base portion is truncated, forming a flat tip end, said major base of said sculptured portion being tapered upwardly through said tip subportion and intersecting said flat tip end, whereby a dental wedge is devised that is easily inserted between said teeth, while preserving the gums, provides a minimum of obstruction to a matrix band disposed on either one of said teeth above said wedge and emits a hemostatic solution to inhibit bleeding of the gums.

2. The improvement of claim 1 wherein said minor base is generally parallel to said major base everywhere through said sculptured portion except in said tip subportion.

* * * * *